US005783439A

United States Patent [19]
Reichler et al.

[11] Patent Number: 5,783,439

[45] Date of Patent: Jul. 21, 1998

[54] FORCED HOT AIR HEATING DEVICE

[75] Inventors: Allen Reichler, Livingston, Tex.; Raymond Cracauer, Plymouth, Minn.

[73] Assignee: Becton Dickinson and Company, Franklin Lakes, N.J.

[21] Appl. No.: 846,395

[22] Filed: Apr. 30, 1997

[51] Int. Cl.$^6$ ..................... C12M 3/00

[52] U.S. Cl. ..................... 435/286.1; 435/286.6; 435/303.1; 435/809

[58] Field of Search ..................... 435/286.1, 286.6, 435/303.1, 809

[56] References Cited

U.S. PATENT DOCUMENTS 5,455,175 10/1995 Wittwer et al. ..................... 435/286.1

5,512,440 4/1996 Down et al. ..................... 435/6

*Primary Examiner*—David A. Redding

*Attorney, Agent, or Firm*—David W. Highet, Esq.

[57] ABSTRACT

A forced air heating apparatus for providing automatic cyclical heating and cooling of biological samples includes a housing and a heating chamber within the housing. The heating chamber supports a biological sample tray for supporting a plurality of sample containers. A heating device and an impeller are provided to heat the heating chamber and to direct heated air over the sample containers. The heating chamber is sealed to prevent escape of materials and includes a vent coupled to a filter to maintain ambient pressure in the heating chamber and trap particulate materials passing through the vent.

33 Claims, 10 Drawing Sheets

FORCED HOT AIR HEATING DEVICE

FIELD OF THE INVENTION

The present invention relates generally to a forced hot air heating device for rapid and uniform heating biological samples. The invention is further directed to a forced hot air heating device for sequential heating and cooling of biological samples and particularly for decontaminating DNA-containing samples and opening DNA to single strand form.

BACKGROUND OF THE INVENTION

Many research and analysis processes require uniform heating of a biological sample to decontaminate the sample. One example of such processes is in the decontamination of samples prior to amplification of target nucleic acid (DNA) sequences in liquid biological samples. The samples are typically very small volumes which require rapid and uniform heating. The devices for the heating require careful timing and temperature control to produce consistent and reliable results.

DNA amplification generally requires lysis of the microorganism and the liberation of the DNA and cellular material. There are numerous detection methods for determining the presence of pathogenic organisms which rely on the lysis of the organism, such as mycobacteria. Numerous procedures exist for the lysis of mycobacteria in the literature. However, many of these methods are labor intensive, and require caustic agents or specialized equipment. Recently, heating procedures for lysing mycobacteria have proved advantageous as disclosed in U.S. Pat. No. 5,512,440. Advances in mycobacteria genetics and interest in pathogens have created a need for efficient processes and equipment for lysing microorganisms and particularly mycobacteria.

Various devices are known for heating biological samples for DNA amplification. Examples of the prior devices used metal heat blocks to cycle the temperature over a controlled time period. It is often difficult to control the temperature changes in these metal blocks to maintain a constant and uniform temperature.

Other known heating devices include a water bath to heat the sample. These devices have met with limited success because the mass of water limits the maximum temperature and creates difficulties in obtaining the temperatures. The water bath limits the heating temperature to 100° C. unless the bath is pressurized. The sample container is usually only partially immersed in the water so that the entire sample may not be heated uniformly. The water bath also requires a number of fluid connections and hoses, thereby increasing cost and maintenance. Other heating devices use heated air to heat the sample. One example is disclosed in U.S. Pat. No. 5,455,175. The thermal cycling device includes a sample chamber for rapidly heating and cooling the samples located therein. This device includes a heating element within the chamber and fan to circulate the air. A door is opened at the end of the heating cycle to exhaust the hot air and draw in cool ambient air.

These prior heating devices for use with heating biological samples, although effective, have met with only limited success. Accordingly, there is a continuing need in the art for efficient and effective heating and cooling devices.

SUMMARY OF THE INVENTION

The present invention is primarily directed to an apparatus for heating and cooling a large number of biological samples at a carefully controlled rate. More particularly, a primary object of the invention is to provide an apparatus for lysing biological samples by quickly and efficiently heating the samples to the required temperature, maintaining a constant and uniform temperature in the samples, and then cooling the samples.

A further object of the invention is to provide an apparatus for lysing biological samples using an enclosed and sealed heating chamber to circulate forced hot air over the sample containers at high velocity to uniformly heat the biological samples and to maintain a uniform temperature throughout the heating chamber.

Another object of the invention is to provide an apparatus having a programmable control unit for operating the apparatus through preselected heating and cool-down cycles.

Still another object of the invention is to provide an apparatus for lysing a biological sample by providing an enclosed and sealed heating chamber with an external heating device and using ambient air to cool the heating chamber.

Another object of the invention is to provide an apparatus for lysing a biological sample by providing an enclosed and sealed heating chamber with an external fan for directing ambient air to cool the heating chamber during a cooling cycle.

A further object of the invention is to provide a forced hot air heating device having a closed heating chamber to prevent the release of pathogens to the atmosphere during the heating/cooling cycle.

Another object of the invention is to provide a forced hot air heating device having a sealed heating chamber and an externally driven fan for circulating hot air within the heating chamber to uniformly heat biological samples where the heating chamber has no openings for the fan.

The objects of the invention are basically attained by providing an apparatus for heating a plurality of biological samples to a selected temperature, the apparatus comprising: a housing having top, bottom, opposite side walls and at least one end wall; a heating chamber positioned in the housing and providing an air space between the housing and an outer surface of the heating chamber, the heating chamber having a sample opening for receiving a plurality of biological samples; a closure member for closing the sample opening in the heating chamber and hermetically sealing the heating chamber; at least one heating element positioned on an outer surface of the heating chamber for heating an interior of the heating chamber; a vent in the heating chamber for maintaining the heating chamber substantially at ambient pressure during a heating cycle; and a filter coupled to the vent for capturing particulate materials escaping from the heating chamber.

The objects of the invention are further attained by providing an apparatus for simultaneously heating a plurality of biological samples, the apparatus comprising: a closed and sealed heating chamber having an access opening; a closure member for closing and hermetically sealing the access opening; a heating element on an external surface of the heating chamber for heating an internal air space of the heating chamber; a vent into the heating chamber for maintaining substantially ambient pressure in the heating chamber when the heating chamber is heated; a filter device coupled to the vent for filtering air passing through the vent; a rotatable and magnetically driven air impeller mounted in the heating chamber for circulating air in the heating chamber; a drive motor on an external surface of the heating chamber, the motor having a rotatable drive magnet for driving the impeller; and a programmable control device for actuating the heating element and drive motor for a selected time period to heat the heating chamber to a predetermined temperature.

These objects of the invention are also attained by providing an apparatus for subjecting biological samples to heating and cooling cycles, the apparatus comprising: a housing having an air inlet for passing cooling air through the housing, the housing further including a top, bottom and opposite side walls, a heating chamber positioned in the housing and being spaced from the top, bottom and opposite side walls for forming a first air channel substantially surrounding the heating chamber, wherein the heating chamber includes a top, opposite side and bottom wall, and a sample opening for receiving the biological samples; a closure member for closing the sample opening in the heating chamber and hermetically sealing the heating chamber; a heating element for heating the heating chamber; an air impeller mounted in the heating chamber for circulating heating air within the heating chamber and uniformly heating the biological samples; a drive motor mounted outside the heating chamber and being magnetically coupled to the air impeller for driving the air impeller; a control device for actuating the heating element and the drive motor to heat the biological sample for a preselected amount of time, and for deactivating the heating element while continuing to circulate air within the heating chamber to cool the heating chamber and biological sample; and a sample tray for supporting a plurality of biological samples, the sample tray being removably received in the heating chamber.

Other objects, advantages and salient features of the invention will become apparent from the following detailed description, which, taken in conjunction with the drawings, discloses a preferred embodiment of the invention.

BRIEF DESCRIPTION OF THE DRAWINGS

Referring to the drawings which form part of this original disclosure.

DETAILED DESCRIPTION OF THE INVENTION

Figure 1:
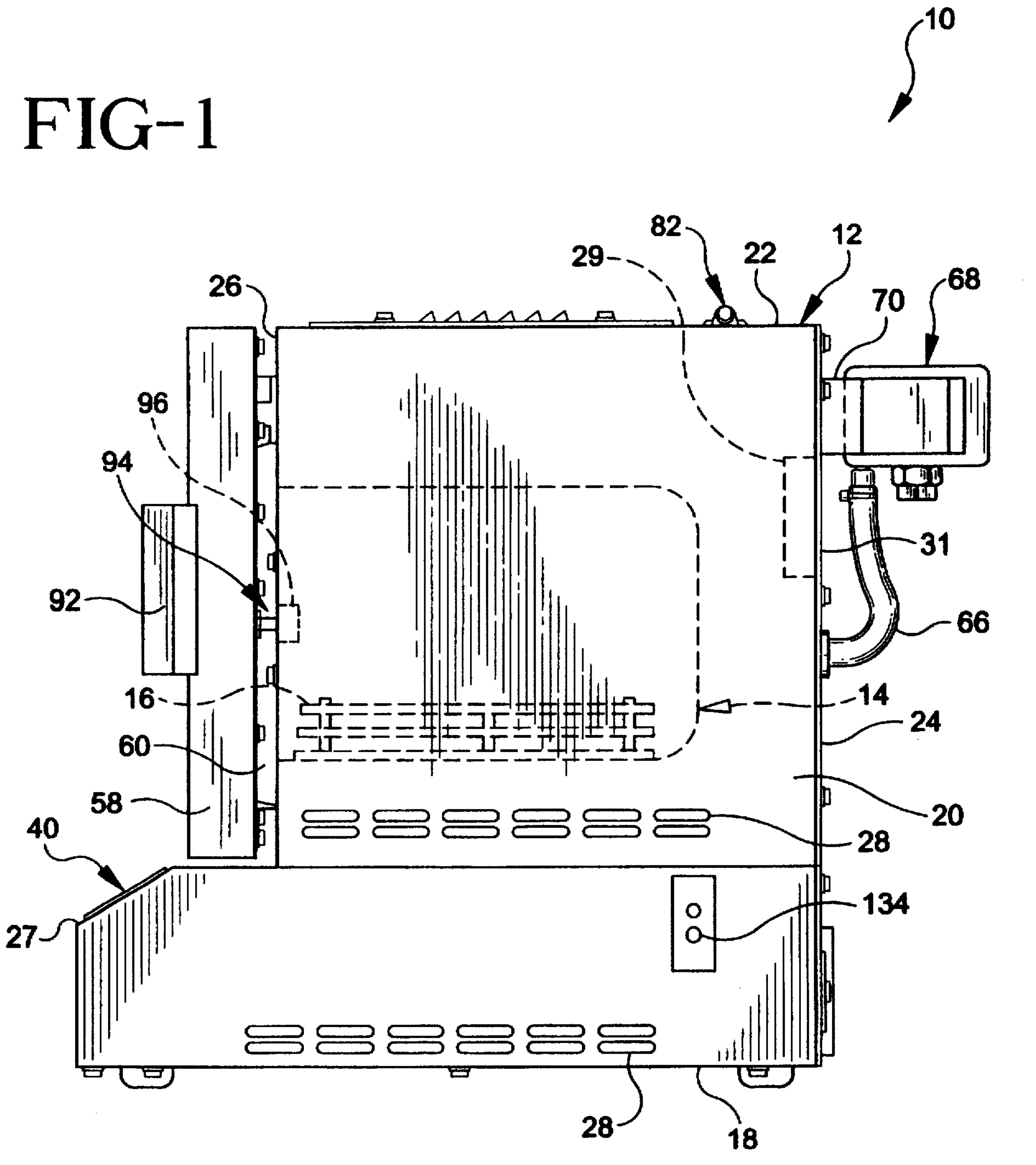
FIG. 1 is a side elevational view of the heating apparatus in a preferred embodiment of the invention.
Figure 2:
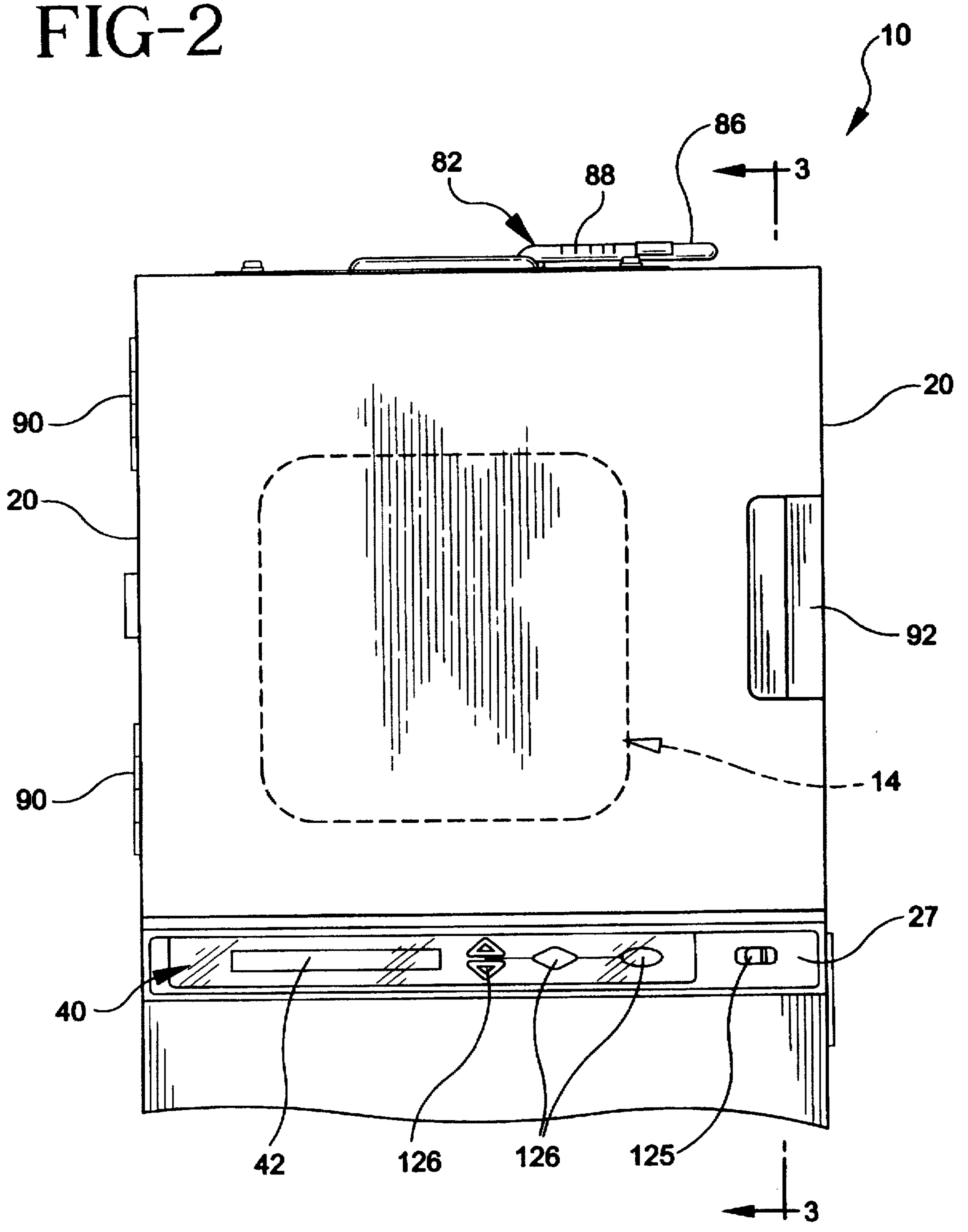
FIG. 2 is a front elevational view of the heating apparatus of FIG. 1.

The present invention is directed to an apparatus for subjecting a plurality of biological samples to controlled cyclical heating and cooling stages. The apparatus subjects the biological samples to forced air heating to rapidly and efficiently control the temperature profile of the samples.

The apparatus of the invention is particularly suitable for the lysis and resultant liberation of DNA and cellular material from biological samples such as, for example, mycobacteria. Lysing of mycobacteria is advantageously carried out using heat rather than other lysing processes. The heat treatment of the biological sample can kill pathogenic organisms or render the organism non-infectious. In addition, lysing with heat can simultaneously liberate intracellular components, open the DNA to single strand form and produce samples that are safe to handle. A suitable method for lysing mycobacteria is disclosed in U.S. Pat. No. 5,512,440 which is hereby incorporated by reference in its entirety.

Referring to the drawings, and particularly to FIGS. 1–5, the forced hot air heating apparatus 10 comprises a housing 12, a heating chamber 14 and a sample rack 16.

The housing 12 forms an enclosure for apparatus 10 and heating chamber 14. Housing 12 is generally formed from sheet metal panels and includes a bottom wall 18, side walls 20, a top wall 22, a rear wall 24 and a front wall 26. A suitable thermal insulation material 36, such as a fiberglass mat, is applied on the side walls 20, top wall 22 and rear wall 24. Side wall 20 includes several apertures 28 to allow free air circulation into the housing 12. Air can be drawn into housing 12 by convection during a cooling cycle to cool heating chamber 14.

In embodiments of the invention, a fan 29 is mounted in housing 12 for operating during a cooling cycle to cool the interior of housing 12 rapidly. During a cooling cycle, fan 29 is actuated to draw air inwardly through apertures 28, around heating chamber 14 and outwardly through exhaust outlets 31. At the end of the cooling cycle, cooling fan 29 is turned off.

A horizontal support plate 30 is mounted in the lower portion of housing 12 to form an upper area 32 and a lower area 34. A thermal insulation 36 is preferably provided on an upper face of support plate 30 to insulate upper area 32. A circuit board including a programmable control unit 38 is mounted in lower area 34 for controlling and actuating apparatus 10 as discussed hereinafter in greater detail.

The front area of housing 12 includes a control pad 40 coupled to control unit 38 by suitable wires or other electrical connection. Control pad 40 is, for example, a membrane switch for controlling and actuating apparatus 10 via control unit 38. A suitable digital display 42 is mounted on front area 27 to cooperate with control pad 40 and control unit 38.

Heating chamber 14 is mounted in upper space 32 within housing 12 and is spaced from side walls 20, top wall 22, horizontal support plate 30 and rear wall 24. Heating chamber 14 has a substantially rectangular shape with top wall 46, bottom wall 48, side walls 50, a rear wall 52 and an open front end 54 to form an open ended cavity. A flange 56 extends outwardly around open end 54. In the preferred embodiment of the invention, heating chamber 14 is an integrally formed unit with no seams, joints or welds. Preferably, heating chamber 14 is made of a thermally conductive material, such as stainless steel formed by deep drawing methods as known in the art. It is preferred to manufacture heating chamber 14 from a single sheet of material to form a sealed heating chamber to reduce the risk of pathogenic material escaping from heating chamber 14 during a heating cycle.

Heating chamber 14 is mounted in housing 12 with flange 56 at front wall 26. A door 58 is mounted on housing 12 for closing open front end 54. A gasket 60 is mounted on flange 56 of heating chamber 14 to mate with door 58 and hermetically seal heating chamber 14.

Figure 3:
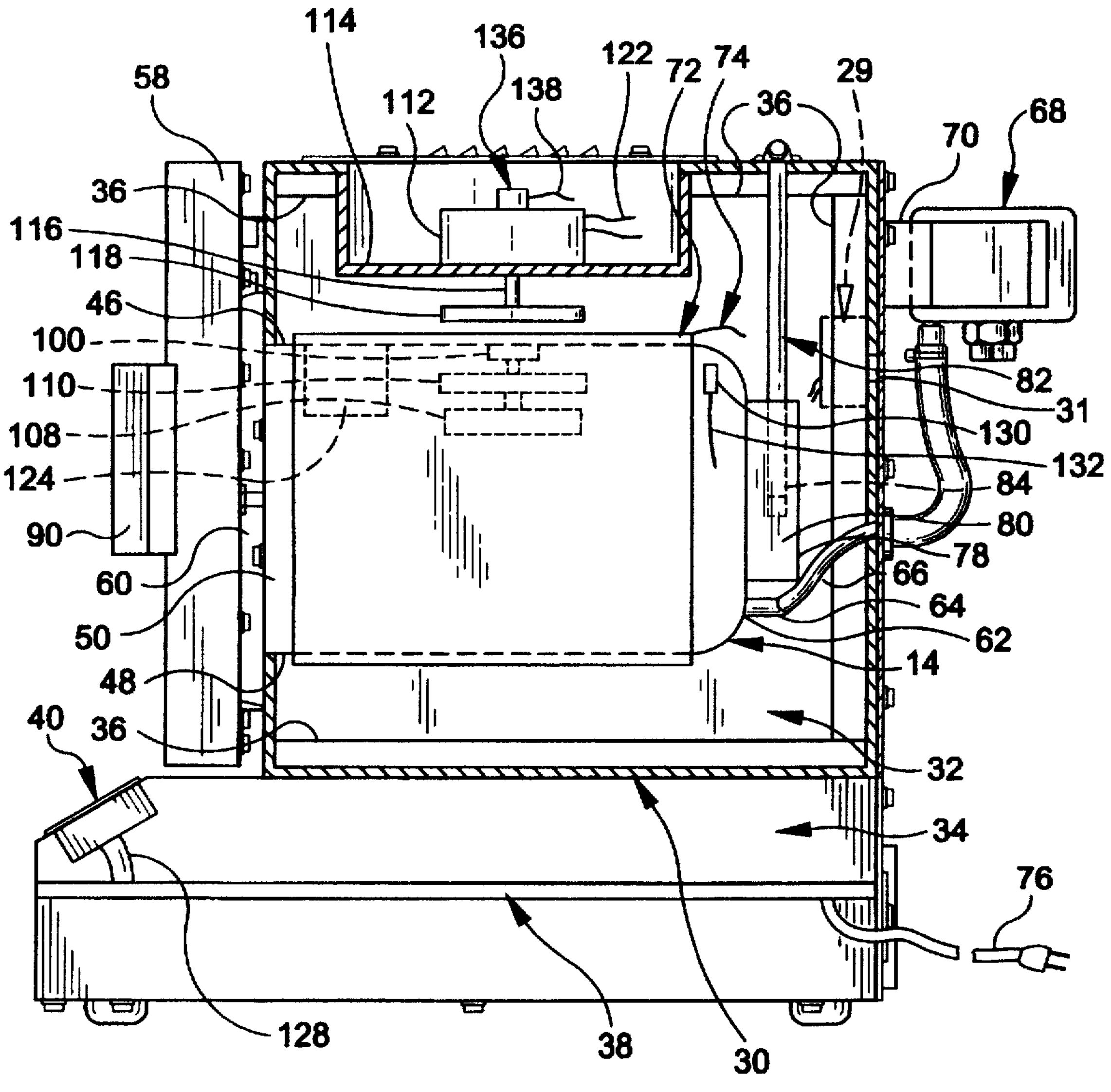
FIG. 3 is a cross-sectional view of the housing taken along line 3—3 of FIG. 2.
Figure 4:
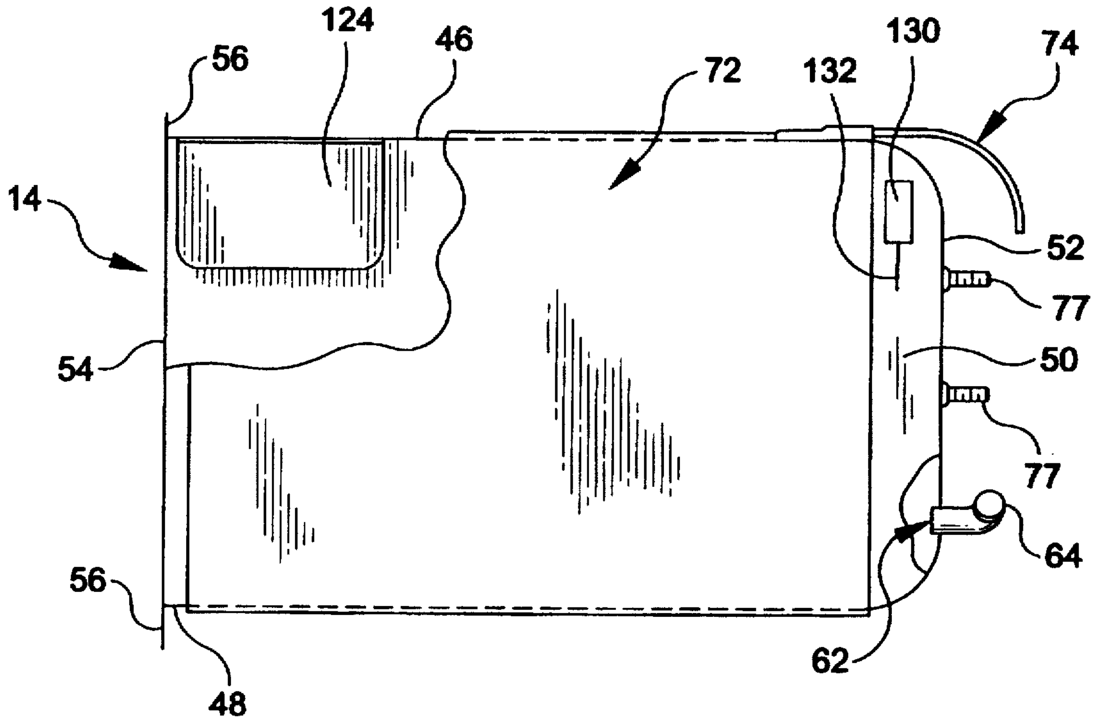
FIG. 4 is a side elevational view of the heating chamber of FIG. 3.
Figure 5:
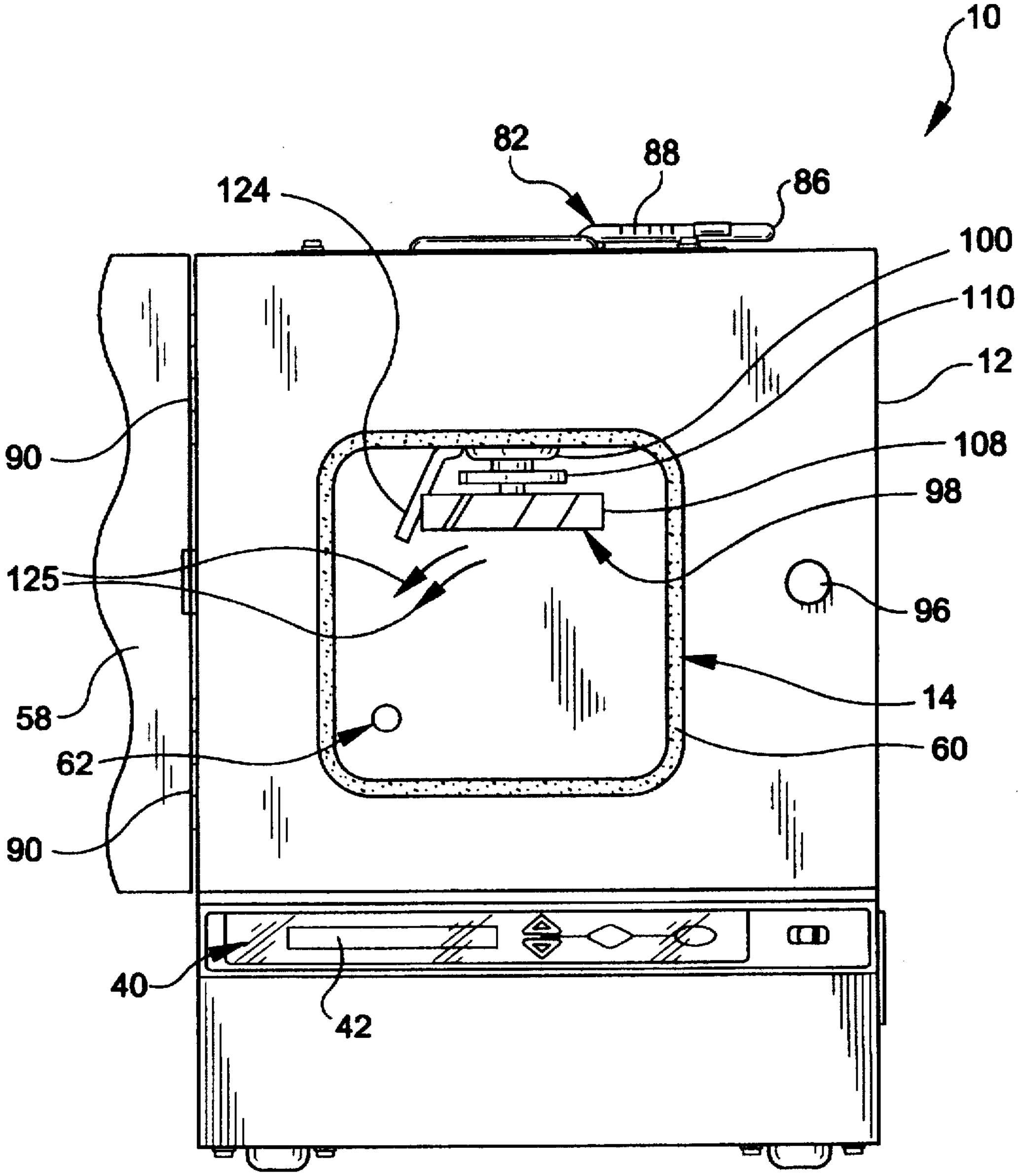
FIG. 5 is a front elevational view of the apparatus of FIG. 1 with the door open.

Heating chamber 14 is preferably sealed by door 58 to contain any material within heating chamber 14 and to prevent infiltration of possible contaminants into the samples being heated during use. When lysing potentially pathogenic materials, it is particularly desirable to provide a hermetically sealed heating chamber to prevent the release of the pathogenic materials to the atmosphere. A vent 62 is provided in the rear wall 52 of heating chamber 14 to maintain heating chamber 14 substantially at ambient pressure, since during the heating phase of heating chamber 14, the air will expand. Vent 62 as shown in FIG. 4 is a tubular section 64 extending through rear wall 52 of heating chamber 14. A separate conduit 66, such as plastic tubing, is coupled to tubular section 64 and to a filter 68. Filter 68, as shown in FIG. 3, is mounted on the outside surface of rear wall 24 of housing 12 by suitable mounting brackets 70. In alternative embodiments, filter 68 can be mounted inside housing 12.

In preferred embodiments, filter 68 is mounted for easy replacement by the user of the apparatus 10. Filter 68 can be any suitable filter for capturing airborne particulate materials and preventing such particulate materials from entering or escaping heating chamber 14. Preferably, filter 68 is a high efficiency particulate air filter (HEPA) as known in the industry. In preferred embodiments, filter 68 is capable of capturing particulates of 0.22 microns or greater while allowing gases such as air and water vapor to pass through. Filter 68 is typically a cartridge-type filter which is able to capture pathogenic materials which may escape from the sample containers during the lysing stage while allowing heated air and water vapor to vent out of heating chamber 14. The door 58 seals the front of heating chamber 14 so that vent 62 provides the only means for particulate materials to escape which are then captured on filter 68. Heating chamber 14 effectively contains any pathogenic materials and captures the pathogenic materials greater than 0.22 microns on filter 68.

Heating chamber 14 includes at least one heating element 72 which is preferably wrapped around top wall 46, side walls 50 and bottom wall 48. In the embodiment illustrated, heating element 72 is a fiberglass mat or mantle having heating members embedded therein and adhesively bonded to the outer surface of heating chamber 14. In further embodiments, heating element 72 can be applied to rear wall 52 of heating chamber 14, but is generally not necessary to provide uniform and efficient heating of heating chamber 14 and biological samples being heated. Heating element 72 includes electrical wires 74 which are connected to control unit 38 and a power source through electrical connector 76. Heating element 72 is connected to control unit 38 for controlling the temperature and timing of the heating operation and cycle of the apparatus 10.

Rear wall 52 of heating chamber 14 includes a pair of mounting screws 77 as shown in FIG. 4 for mounting a thermometer housing 78. Thermometer housing 78 is preferably filled with a thermal grease 80 or other thermally conductive material. A thermometer 82 has a lower end 84 positioned inside thermometer housing 78 and an upper end 86 extending through housing 12. Upper end 86 of thermometer 82 is provided with a visually readable scale 88 to visually determine and verify the temperature of heating chamber 14.

Door 58 is mounted on front wall 26 of housing 12 by hinges 90. A handle 92 and latching mechanism 94 are provided to lock door 58 in the closed position. As shown in FIG. 1, door 58 contacts gasket 60 to seal the front end 54 of heating chamber 14. Latch mechanism 94 is connected to and actuated by a locking control unit 96 to limit access to heating chamber 14. Locking control unit 96 is coupled to and activated by control unit 38 to lock door 58 in the closed position during a heating cycle and unlock door 58 only when heating chamber 14 has completed a heating cycle and has cooled to a safe temperature whereby the samples can be handled. Door 58 can include an override mechanism to enable the operator to open the door 58 when the locking control unit 96 does not unlock door 58 for any reason.

Figure 6:
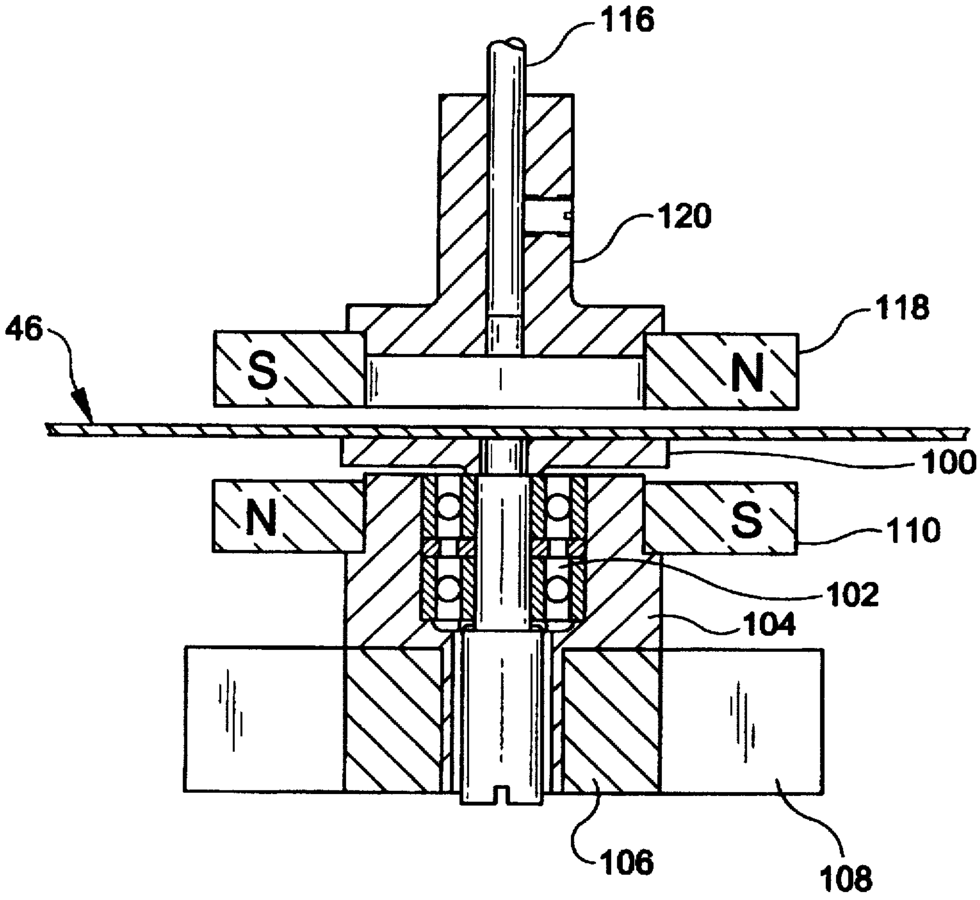
FIG. 6 is a cross-sectional view of the fan assembly of FIG. 3.

Heating chamber 14 includes an impeller and fan assembly 98 to circulate air inside heating chamber 14 and maintain a uniform heat distribution throughout a heating and cooling cycle. Fan assembly 98 as shown in FIG. 6 is preferably an internally mounted assembly to eliminate any openings in heating chamber 14 to maintain a sealed enclosure. Preferably, there are no seals or shafts extending through the wall of heating chamber 14 to eliminate openings or potential leaks which could result in the release of pathogenic materials. In preferred embodiments, fan assembly 98 is a magnetically driven and operated fan which is magnetically coupled to a suitable drive motor. This assembly avoids the need for rotating seals and increases the reliability to maintain a sealed heating chamber. Fan assembly 98 includes a mounting plate 100 attached to an inside surface of upper wall 46 of heating chamber 14. Mounting plate 100 supports a bearing 102 which is coupled to a hub 104 for rotating about an axis of mounting plate 100. An impeller or fan hub 106 having a plurality of fan blades 108 is coupled to hub 104. A disc shaped magnet 110 is also coupled to hub 104 and is closely spaced to upper wall 46. Disc magnet 110 includes areas of alternating polarities as shown in FIG. 6.

Fan assembly 98 further includes a drive motor 112 mounted on a bracket 114 coupled to top wall 22 of housing 12. Drive motor 112 includes a vertical shaft 116 having a drive disc magnet 118 coupled to the lower end by a hub 120. Disc magnet 118 includes areas of alternating polarities and is closely spaced to upper wall 46 of heating chamber 14. Drive motor 112 is electrically coupled to control unit 38 and to a suitable power source by wires 122. Control unit 38 actuates drive motor 112 throughout the entire heating and cooling cycles.

In operation, drive motor 112 rotates drive disc magnet 118 so that opposite polarities on fan disc magnet 110 drive fan 106. Fan blades 108 circulate air inside heating chamber 14 at sufficient velocity to provide a uniform heat distribution throughout the entire heating chamber. An internal deflector plate 124 is mounted adjacent fan assembly 98 on upper wall 46 of heating chamber 14. Preferably, deflector plate 124 is angled with respect to upper wall 46 to produce a downward turbulent air flow as shown by arrows 125 and to uniformly heat the inside space of heating chamber 14. Deflector plate 124, heating element 72 and fan assembly 98 preferably are able to heat the heating chamber 14 to at least about 105° C. in about 10 minutes and provide a less than 1° C. temperature variation at all points in heating chamber 14. Uniform heat distribution is important when heating a plurality of samples to ensure uniform heating of each sample.

Figure 10:
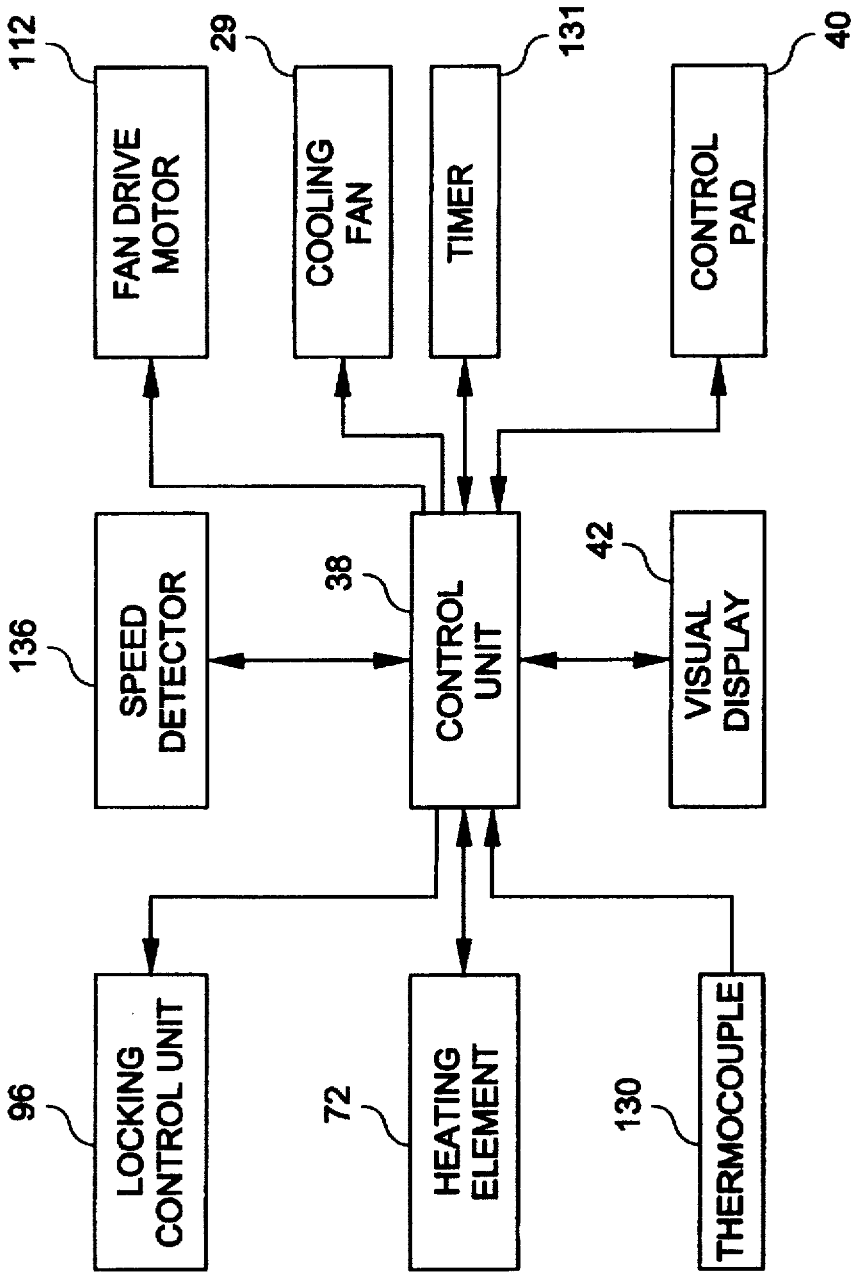
FIG. 10 is a block diagram of the control unit of the heating apparatus.

Control unit 38 includes a suitable microprocessor unit to operate and control assembly 10 as shown in the block diagram of FIG. 10. Control unit 38 is coupled to control pad 40 so that the operator is able to select a preprogrammed timing and temperature sequence by the use of switch 125, selector buttons 126 and connection 128 or to enter a desired time and temperature into the microprocessor. Digital display 40 cooperates with control unit 38 and a timer 131 to display various available preprogrammed heating cycles and to display the entered information by the operator. Control unit 38 is also coupled to latch mechanism 94 by the locking control unit 96, fan drive motor 122, cooling fan 29 and to a thermocouple 130. Fan drive motor 122 is actuated by control unit 38 and the microprocessor throughout the heating and cooling cycle. Cooling fan 29 can be actuated by control unit 38 during the cooling cycle to rapidly cool the housing 12 and heating chamber 14.

The microprocessor of control unit 38 also actuates locking control unit 96 to prevent door 58 from being opened until the end of a heating and cooling cycle. Locking control unit 96 verifies that door 58 is properly closed and prevents the heating cycle from being initiated when the door is ajar or not properly closed. Thermocouple 130 is mounted on heating chamber 14 and connected to control unit 38 by wires 132 to monitor and control the temperature of heating chamber 14. Thermocouple 130 is also coupled to external connector 134 for coupling to an auxiliary digital temperature display as desired (not shown).

Fan drive motor 112 includes a speed detector 136 which is connected to the control unit 38 by wires 138 or other suitable electrical connection to monitor the variations in the speed of motor 112. In normal operations, fan drive motor 112 is magnetically coupled to fan 108 such that fan 108 produces a normal load on motor 112 and causes motor 112 to operate at a normal operating speed. This normal drive motor speed is detected by speed detector 136 and control unit 38 as a normal operating function. If the drive magnet 118 fails to couple properly with fan magnet 110 or there is an obstruction preventing fan blades 108 from turning, drive motor 112 will still continue to turn. When fan blades 108 are not turning, the load on drive motor 112 will be different than under the normal operating conditions. This difference in load will translate into a different operating speed of drive motor 112 which is detected as a speed variation by speed detector 136 and control unit 38. A visual or audio signal can then be produced by a signal indicator of control unit 38 so that the operator can correct the failure of the fan to rotate. Often, simply stopping and restarting drive motor 112 is sufficient to properly engage fan magnet 110.

Figure 7:
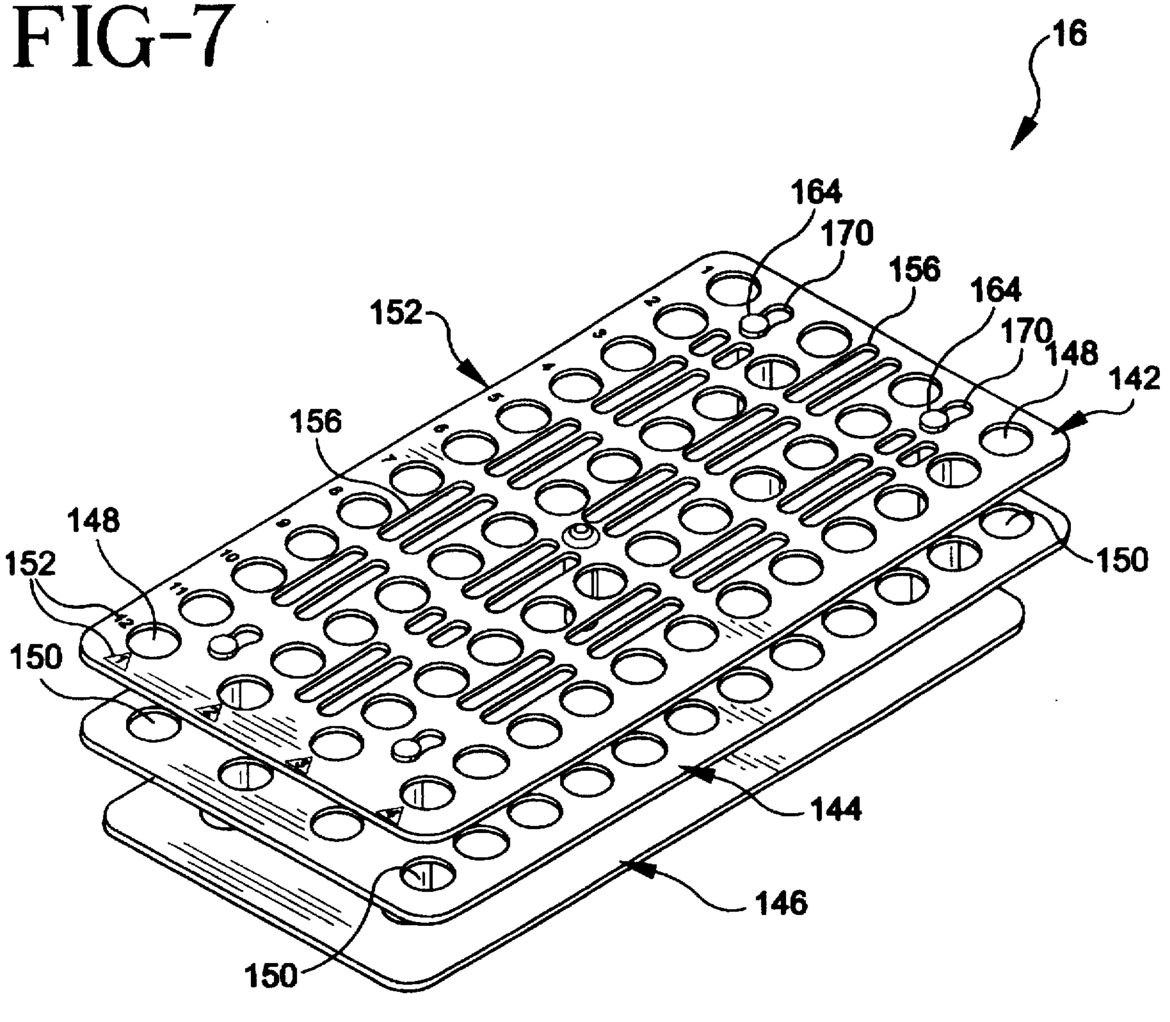
FIG. 7 is a perspective view of the rack in a preferred embodiment of the invention.
Figure 8:
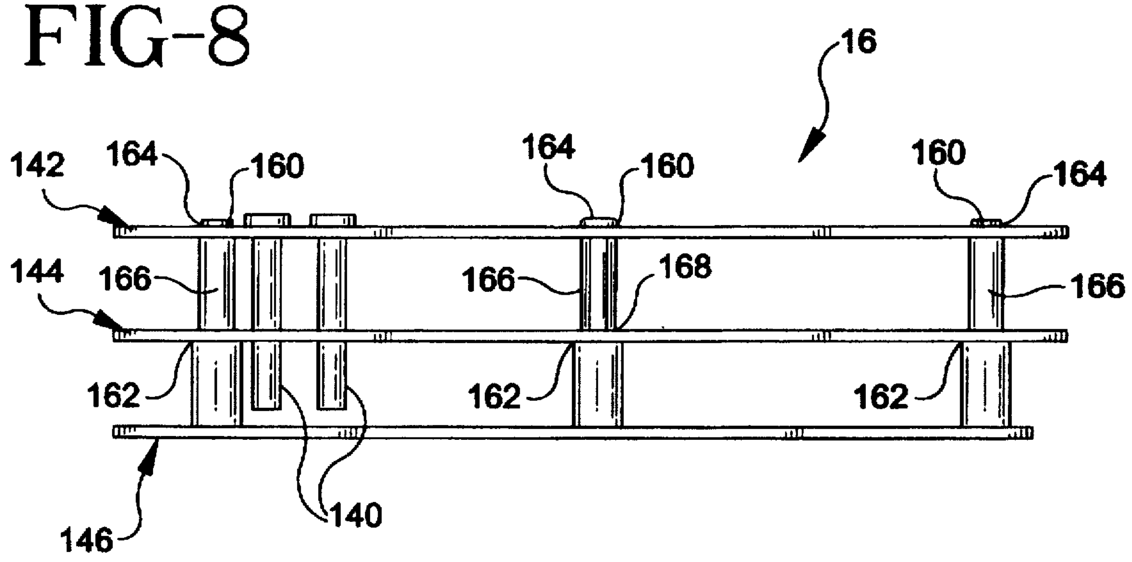
FIG. 8 is a side elevational view of the rack of FIG. 7.
Figure 9:
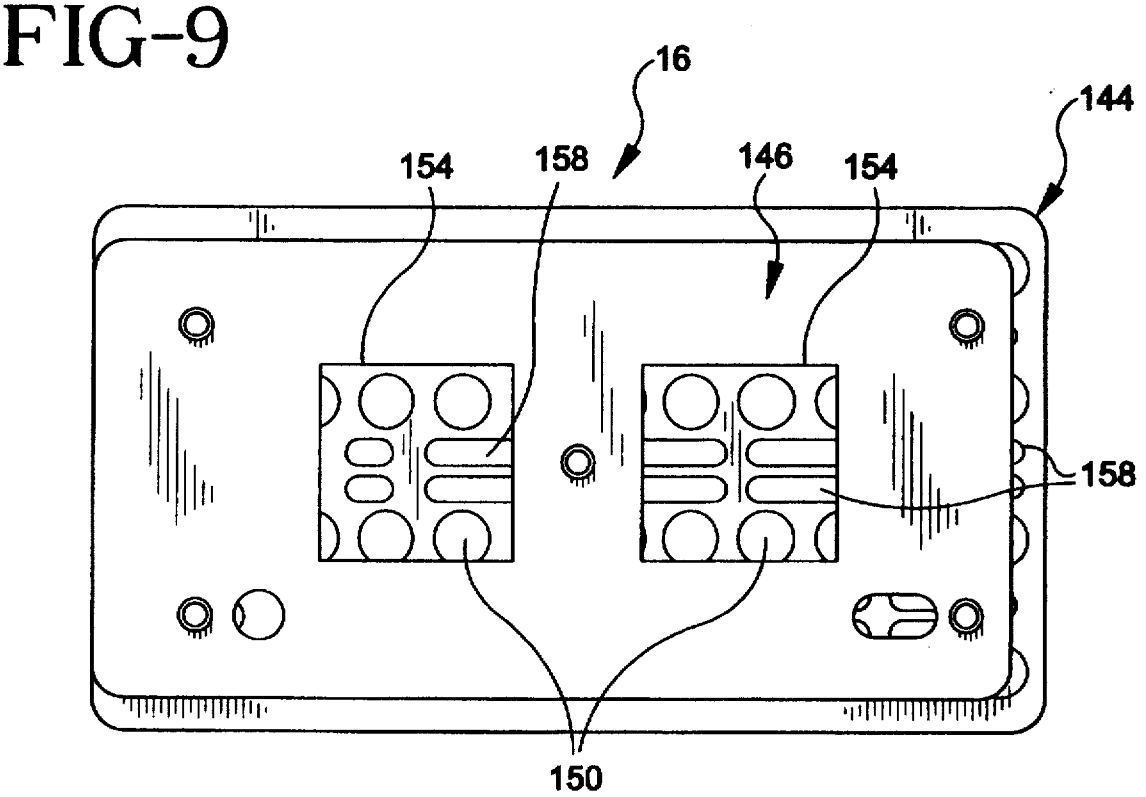
FIG. 9 is a bottom view of the rack of FIG. 7.

Referring to FIGS. 7–9, rack 16 is capable of holding a plurality of sample containers 140. Sample containers 140 are standard vials used in the industry for lysing microbiological samples. Suitable sample containers are, for example, microcentrifuge tubes as known in the art. Rack 16 as shown in FIGS. 7–9 includes a top plate 142, middle plate 144, and bottom plate 146 designed to allow maximum air flow around the sample containers 140 to uniformly heat and cool sample containers 140. Top plate 142 and middle plate 144 include a plurality of superimposed holes 148,150, respectively for receiving and supporting sample containers 140. Holes 148,150 in top and middle plate 142,144, respectively, are arranged in rows and columns which are identified by suitable indicia 152 on top plate 142 to identify a particular sample. In the embodiment shown, holes 148, 150 are provided to receive sample containers 140 in four rows of twelve. Bottom plate 146 includes two large, spaced-apart holes 154 to allow air flow around sample containers 140. Top plate 142 and middle plate 144 include a plurality of elongated slots 156,158, respectively, to promote air circulation and uniform heating and cooling.

Bottom plate 146 includes a plurality of posts 160 having a shoulder 162 and a head 164 as shown in FIG. 8. Middle plate 144 includes holes 168 aligned with posts 160 so that plate 144 is supported on shoulder 162. A sleeve 166 is then placed over posts 160 to maintain the position of middle plate 144. Top plate 142 includes a plurality of key hole slots 168 for engaging heads 164 and securing rack 16 in an assembled condition. Rack 16 can be disassembled as needed for cleaning and repair.

The forced hot air heating apparatus 10 of the invention preferably includes programmable control unit 38 for storing a plurality of heating and cooling protocols for lysing different samples. The operator is able to select the desired heating and cooling protocol by use of the selector buttons 126 on the display and control panel 40. Control unit 38 actuates the selected heating cycle and prevents opening of the door or terminating the heating cycle prematurely to ensure that complete lysis of the sample occurs.

In use, the samples to be lysed are prepared in suitable sample containers 140 or ampoules sealed with a closure member and placed in the rack 16. Rack 16 is then placed in heating chamber 14 and door 58 is closed. Referring to the flow chart of FIG. 11, a heating and cooling protocol is selected from the preprogrammed protocols as indicated by block 170 or by entering the desired protocol. When the heating and cooling protocol is initiated, locking mechanism 94 locks door 58 in the closed position and verifies that the door is locked as indicated in block 172 until the heating and cooling is completed. If the door is ajar, the operator is informed as indicated in block 174 by a visual or audible signal. In preferred embodiments of the invention, control unit 38 locks door 58 to prevent the door from being opened until the heating chamber and the samples cool to a suitable temperature, typically about 40° C., to provide safe handling.

Figure 11:
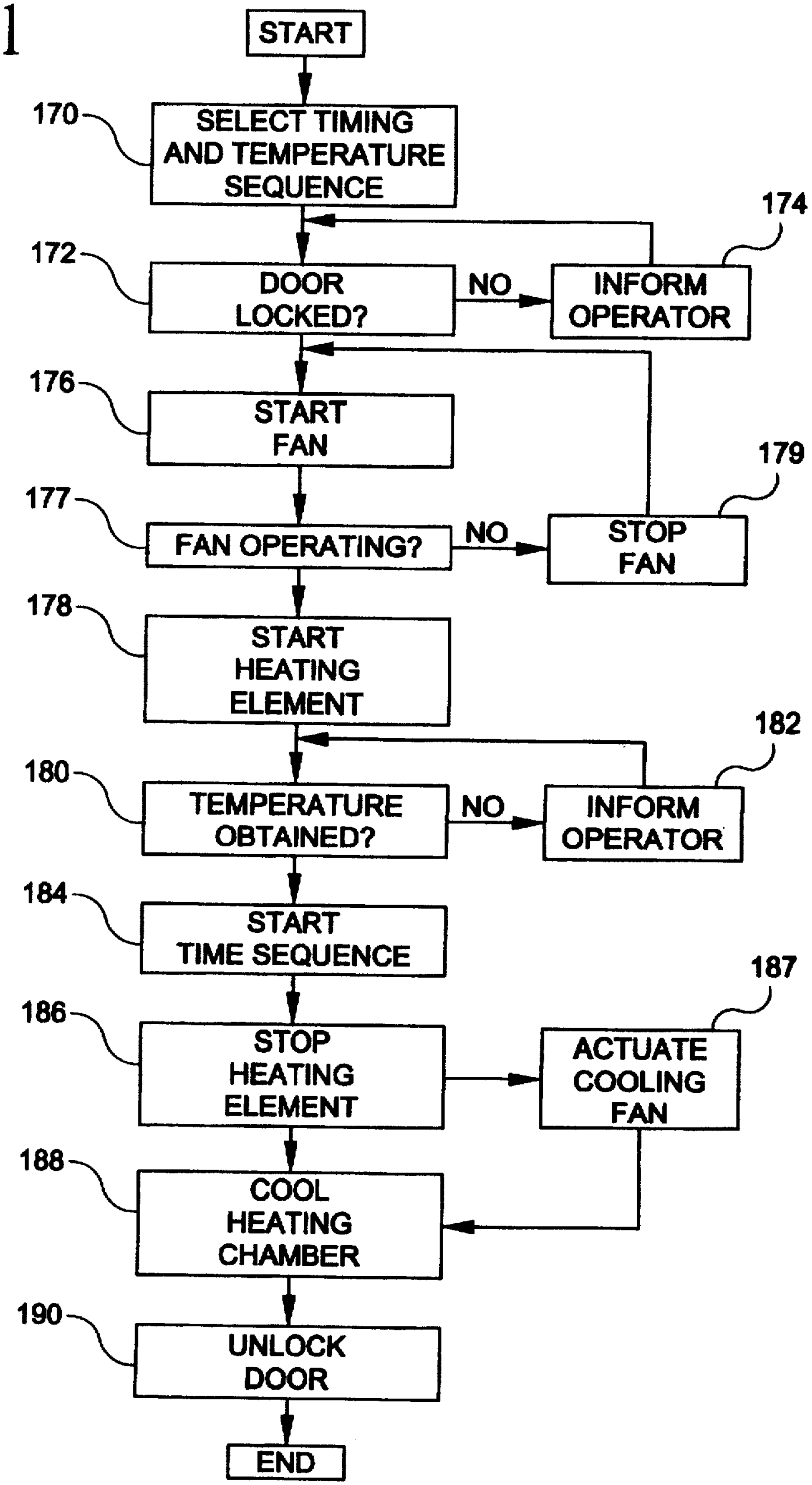
FIG. 11 is a flow chart of the heating and cooling phases of the apparatus.

Control unit 38 actuates fan drive motor as indicated in block 176 of the flow chart of FIG. 11. The fan rotation is verified as indicated in block 177 which stops the motor in block 179 when the fan is not turning. The fan motor is restarted as indicated in block 176. The heating elements are then actuated as indicated in block 178 to heat the heating chamber. Fan drive motor 112 continues to circulate the hot air throughout the heating cycle within heating chamber 14. The desired operating temperature of heating chamber 14 for a selected heating cycle is detected as indicated in block 180. The operator is informed as indicated in block 182 if the selected temperature is not obtained. The timing sequence as shown in block 184 is initiated after the temperature is obtained. At the end of the heating cycle, control unit 38 turns off heating element 72 as shown in block 186. During the cooling cycle, room temperature air can be drawn into housing 12 around heating chamber 14 by actuating fan 29 as indicated in block 189 or by natural convection of air through housing 12. The cooling air dissipates the heat and allows heating chamber 14 to cool as indicated in block 188 while continuing the operation of fan 108 to maintain uniform air circulation around sample containers 140 so that sample containers 140 cool uniformly. It is preferred to operate circulating fan 108 continuously to maintain a uniform heat distribution throughout the heating and cooling cycles. The temperature variation in heating chamber 14 and sample containers 140 is preferably less than 1° C. at all times. At the end of the cooling step, the door is unlocked as indicated in block 190.

In addition to the preprogrammed heating and cooling cycles, control unit 38 preferably has a preprogrammed decontamination cycle. The decontamination cycle is capable of heating the heating chamber 14 to temperatures of about 120°–140° C. for a predetermined length of time, typically about 45 minutes, to effectively decontaminate the heating chamber 14.

The heating element 72 for heating chamber 14 is preferably a high efficiency unit capable of heating to a temperature of 105° C. within about 10 minutes. Preferably, control unit 38 and heating element 72 uniformly heat heating chamber 14 within about 5° C. of the temperature selected by the control unit 38. During a lysolyzation cycle it is desirable to heat the heating chamber uniformly to about 105° C. for 30 minutes. The cooling cycle allows the heating chamber 14 to cool to about 40° C. within about 10 minutes by deactivating heating element 72 and allowing room temperature air to flow through housing 12 and around heating chamber 14.

The cellular components liberated by lysis using the present invention can be used for various processes including the identification of mycobacteria and amplification of nucleic acid by known methods such as polymerase chain reaction (PCR), strand displacement amplification (SDA) and ligase chain reaction.

Once a sample is heated, the marker or identifying agent is added. Depending on the marker selected, the presence of mycobacteria can be detected by various methods as known in the art. Other detection methods include Southern Blot analysis and electrophoretic gel visualization, which can take place with or without prior amplification.

Mycobacteria are isolated from a variety of sources including feces, sputum, urine, serum, tissue and other body fluids. The cells are usually isolated using known processes and pelleted by centrifugation and placed in suspension. The cell suspension is then subjected to a heat treatment typically in the range of about 60° C. to about 100° C. The heat range for a particular organism is obtained by titrating heat within this range against release of desired target molecules from the organism. The heat will lyse the organism with subsequent release of intracellular components.

The heating apparatus of the invention is particularly suitable for obtaining DNA from an organism in single strand form. A variety of amplification methods then can be performed on the resulting sample as known in the art.

The heating time for obtaining the intracellular components range from two minutes to about twenty minutes. The amount of heat and time of heat is readily determined by sampling a portion of the mycobacteria to be lysed and examined for signs of lysis such as detection of intracellular components. This determined heating time can be used to program heating device 10.

A suitable protocol for lysing mycobacteria with heat includes centrifuging the sample of mycobacteria and discarding the supernant. The pellet of mycobacteria can then be reconstituted in a buffered mixture in the heating device 10 and heated to lyse the sample.

While an advantageous embodiment has been chosen to illustrate the invention, it will be understood by those skilled in the art that various changes and modifications can be made therein without departing from the scope of the invention as defined in the appended claims.

What is claimed is:

1. An apparatus for heating biological samples to a selected temperature, said apparatus comprising:

a housing having top, bottom, opposite side walls and at least one end wall, said housing having at least one air inlet for receiving outside air into said housing;

a heating chamber positioned in said housing and providing an air space between said housing and an outer surface of said heating chamber, said heating chamber having a sample opening for receiving biological samples;

a closure member for closing said sample opening in said heating chamber and hermetically sealing said heating chamber;

at least one heating element positioned on an outer surface of said heating chamber for heating an interior of said heating chamber;

a vent in said heating chamber for maintaining said heating chamber substantially at ambient pressure during a heating cycle; and a filter coupled to said vent for capturing particulate materials escaping from said heating chamber.

2. The apparatus of claim 1, wherein said filter is a particulate air filter for capturing particles of 0.22 microns or larger.

3. The apparatus of claim 1, further comprising a cooling fan for drawing cooling air into said housing to cool said heating chamber during a cooling cycle.

4. The apparatus of claim 1, wherein said heating chamber is stainless steel.

5. The apparatus of claim 1, wherein said heating chamber comprises an integrally formed top wall, a bottom wall, two opposite side walls, and a rear wall defining an open ended cavity, wherein said open ended cavity is closed by said closure member.

6. The apparatus of claim 5, wherein said vent comprises a conduit extending from one of said walls to said filter.

7. The apparatus of claim 1, wherein said at least one heating element substantially surrounds said heating chamber.

8. The apparatus of claim 5, wherein said at least one heating element contacts said top, bottom and opposite side walls.

9. The apparatus of claim 1, further comprising at least one air impeller disposed in said heating chamber for uniformly circulating air in said heating chamber.

10. The apparatus of claim 1, wherein said impeller is driven by a motor mounted adjacent an external surface of said heating chamber.

11. The apparatus of claim 10, wherein said motor comprises a rotatable drive magnet and said impeller comprises a rotatable magnet rotatably driven by said drive magnet.

12. The apparatus of claim 11, further comprising a speed detection device coupled to said motor and a signal indicator device for indicating a first speed of said motor when said impeller is rotating and for indicating a second speed of said motor when said impeller is not being driven by said motor.

13. The apparatus of claim 9, further comprising at least one air deflector positioned in said heating chamber for dispersing circulating air in said heating chamber.

14. The apparatus of claim 1, further comprising:

a lock for locking said closure member in a closed position; and a lock control unit, coupled to said lock, for actuating said lock.

15. The apparatus of claim 1, further comprising a rack removably received in said heating chamber, said rack having a base member and a member spaced from said base member and having a plurality of first holes for receiving sample containers, said base and top member having a plurality of second holes for uniformly circulating hot air around said sample containers.

16. The apparatus of claim 1, further comprising a temperature sensing device coupled to an outer surface of said heating chamber, for sensing a temperature of said heating chamber.

17. The apparatus of claim 1, further comprising a control unit for actuating said heating element and said drive motor for a preselected amount of time during a heating cycle to heat said biological samples at a first preselected temperature, and for deactivating said heating element and continuing actuation of said drive motor to circulate air in said heating chamber during a cooling cycle until a selected second temperature is obtained.

18. An apparatus for heating biological samples, said apparatus comprising:

a closed and sealed heating chamber having an access opening;

a closure member for closing and hermetically sealing said access opening;

a heating element on an external surface of said heating chamber for heating an internal air space of said heating chamber;

a vent in said heating chamber for maintaining substantially ambient pressure in said heating chamber when said heating chamber is heated;

a filter device coupled to said vent for filtering gases passing through said vent and collecting particulate materials from said gases;

a rotatable and magnetically driven air impeller mounted in said heating chamber for circulating air in said heating chamber;

a drive motor adjacent an external surface of said heating chamber, said drive motor having a rotatable drive magnet for driving said impeller; and a programmable control device for actuating said heating element and drive motor for a selected time period to heat said heating chamber to a predetermined first temperature during a heating cycle and for deactivating said heating element during a cooling cycle.

19. The apparatus of claim 18, wherein said heating chamber is an integrally formed member having a top wall, a bottom wall, two opposite side walls and a rear wall, wherein said heating element surrounds said top, side and bottom walls and said vent extends through said rear wall.

20. The apparatus of claim 18, further comprising a conduit extending from said vent to said filter device, and wherein said filter device is a particulate air filter for capturing particulates of 0.22 microns or larger.

21. The apparatus of claim 18, further comprising a mounting bracket for supporting said drive motor and spacing said drive motor and drive magnet from said heating chamber.

22. The apparatus of claim 18, further comprising an air deflector in said heating chamber for deflecting air circulating in said heating chamber.

23. The apparatus of claim 18, further comprising a lock, for locking said closure member, wherein said lock is actuated by said control device for preventing opening of said closure member until a predetermined heating cycle is completed and said heating chamber cools to a second temperature.

24. The apparatus of claim 18, further comprising a temperature sensing device coupled to an external surface of said heating chamber.

25. The apparatus of claim 18, further comprising a cooling fan for passing cooling air through said housing and around said heating chamber during a cooling cycle to cool said heating chamber.

26. The apparatus of claim 18, further comprising:

a speed detection device coupled to said drive motor for detecting motor speed; and a signal device, coupled to said speed detection device and to said control device, for producing a first signal when said motor and impeller are rotating and a second signal when said motor rotates and said impeller does not rotate.

27. An apparatus for subjecting biological samples to heating and cooling cycles, said apparatus comprising:

a housing having an air inlet for passing cooling air through said housing, said housing further including a top, bottom and opposite side walls;

a heating chamber positioned in said housing and being spaced from said top, bottom and opposite side walls for forming a first air channel substantially surrounding said heating chamber, wherein said heating chamber includes a top and bottom wall, and a sample opening for receiving said biological samples;

a closure member for closing said sample opening in said heating chamber and hermetically sealing said heating chamber;

a heating element for heating said heating chamber;

an air impeller mounted in said heating chamber for circulating heating air within said heating chamber and uniformly heating said biological samples;

a drive motor mounted outside said heating chamber and being magnetically coupled to said air impeller for driving said air impeller;

a control device for actuating said heating element and said drive motor to heat said biological sample for a preselected amount of time during a heating cycle, and for deactivating said heating element while continuing actuation of said drive motor during a cooling cycle to circulate air within said heating chamber to cool said heating chamber and biological sample; and a sample tray for supporting a plurality of biological samples, said sample tray being removably received in said heating chamber.

28. The apparatus of claim 27, further comprising:

a vent in said heating chamber for maintaining substantially ambient pressure in said heating chamber; and a particulate air filter coupled to said vent for capturing particulate materials of 0.22 microns or larger vented through said vent.

29. The apparatus of claim 27, further comprising an air deflector in said heating chamber for deflecting moving air from said impeller.

30. The apparatus of claim 29, wherein said air deflector is positioned adjacent said air impeller for directing air toward said bottom wall of said heating chamber.

31. The apparatus of claim 29, further comprising a lock for locking said closure member, wherein said lock is actuated by said control device for preventing opening of said closure member until a heating and cooling cycle is completed.

32. The apparatus of claim 29, further comprising a cooling fan for drawing cooling air through said housing to cool said heating chamber, said cooling fan being coupled to said control device and being actuated during a cooling cycle.

33. The apparatus of claim 29, further comprising a speed detection device coupled to said motor and a signal indicator device for indicating a first speed of said motor when said impeller is rotating and for indicating a second speed of said motor when said impeller is not being driven by said motor.

* * * * *